United States Patent [19]
Caviezel

[11] Patent Number: 5,665,602
[45] Date of Patent: Sep. 9, 1997

[54] METHOD FOR THE DETERMINATION OF THE FAT CONTENT OF SAMPLES, PREFERABLY ORGANIC SAMPLES

[75] Inventor: Rafael Caviezel, Saas, Switzerland

[73] Assignee: Buchi Labortechnik AG, Flawil, Switzerland

[21] Appl. No.: 555,791

[22] Filed: Nov. 9, 1995

[30] Foreign Application Priority Data

Sep. 4, 1995 [CH] Switzerland ............... 2507/95

[51] Int. Cl.$^6$ ................................. G01N 33/92
[52] U.S. Cl. .................. 436/71; 436/20; 436/23; 436/154; 436/161; 436/171; 436/174; 436/175; 436/177; 436/178
[58] Field of Search .................. 436/20, 23, 71, 436/161, 171, 174, 175, 177, 178, 154

[56] References Cited

U.S. PATENT DOCUMENTS

| | | | |
|---|---|---|---|
| 1,841,672 | 1/1932 | Petersen | 436/23 X |
| 3,351,431 | 11/1967 | Berry | 436/22 |
| 4,377,641 | 3/1983 | Dee et al. | 436/178 |
| 4,753,889 | 6/1988 | Collins | 436/23 |
| 4,980,295 | 12/1990 | Udy | 436/21 |
| 5,017,614 | 5/1991 | Pariza et al. | 514/558 |
| 5,196,169 | 3/1993 | Schick et al. | 422/81 |
| 5,496,735 | 3/1996 | Schwertner | 436/71 |

FOREIGN PATENT DOCUMENTS

| | | |
|---|---|---|
| 49-015238 | 4/1974 | Japan. |
| 49-15238 | 4/1974 | Japan. |
| 519633 | 8/1976 | U.S.S.R. |
| 824054 | 4/1981 | U.S.S.R. |
| 1054777 | 11/1983 | U.S.S.R. |
| 1354106 | 11/1987 | U.S.S.R. |
| 0000715 | of 1906 | United Kingdom. |

OTHER PUBLICATIONS

*Quantitative Chemical Analysis*, 2nd Edition, Harris, 1987, p. 756.

*The Condensed Chemical Dictionary*, 10th Edition, Hawley, 1981, p. 909.

Primary Examiner—Jill Warden
Assistant Examiner—Sharidan Carrillo
Attorney, Agent, or Firm—Shoemaker and Mattare, Ltd.

[57] ABSTRACT

In a method for the determination of the fat content of samples, preferably organic samples, fat portions are dissolved out of the sample by means of extraction. A high boiling point solvent is used for extraction. Through the use of a high boiling point solvent, all possible fat portions will be dissolved out and the extraction time will be significantly reduced. Concurrent with extraction, the extracted fat portions are saponified through the addition of a base, as a result of which salts of the fatty acids contained in the sample will be formed. In further procedural steps, these salts of the fatty acids are subjected to further treatment, separated from one another and analysed. The method enables the exact determination of the fat content of organic samples on the basis of the fatty acids contained within the sample.

14 Claims, 6 Drawing Sheets

METHOD FOR THE DETERMINATION OF THE FAT CONTENT OF SAMPLES, PREFERABLY ORGANIC SAMPLES

BACKGROUND OF THE INVENTION

The invention concerns a method for determining the fat content in samples, preferably organic samples, for example foodstuffs. Due to the legal requirements with regard to the stating of contents in the case of foodstuffs, the determination of fat content is of increasing significance. From the point of view of the physiology of nutrition, the detection of the total fatty acids contained by a food product is of interest: only the determination of fat content on the basis of fatty acids will enable a definitive assessment of the fat calorific value of foodstuffs.

A state of the art method for the determination of fat is based on extraction of fat from the sample with the aid of an organic solvent. Here, for example, direct extraction according to Soxhlet can be mentioned. Extraction after disintegration by means of either an acid or a base (Webull-Stoldt, Rose-Gottlieb) is also known. All these classic methods have various disadvantages. In the main, they are relatively complicated and time-consuming in their application, and are suited only to the determination of fat content in a particular kind of sample. A disadvantage common to all these methods is that the fat is not determined on the basis of fatty acids. Thus, from the point of view of the physiology of nutrition, no definitive results can be obtained.

Methods are also known where the fat portion extracted from the sample is separated into the fatty acids corresponding to the fat by means of saponification and subsequent acidification. These fatty acids are esterified and determined by means of chromatography. In this way, the proportion of each fatty acid within the total fat content can be determined. The disadvantage of this method is that it requires many working steps, With determination being achieved only after a long period of time. In addition, it is not necessary to know the distribution of individual fatty acids when determining the total fat content of foodstuffs. Apart from that, with this state of the art extraction method, the fats are not selectively extracted from the sample.

SUMMARY OF THE INVENTION

The invention has the purpose therefore of avoiding the disadvantages of the state of the art methods, in particular therefore of creating a method of determining the fat content of samples, preferably organic samples, that is rapidly and reliably carried out and enables determination of fat on the basis of all the fatty acids contained within the sample. According to the invention, this purpose is fulfilled with a method according to claim 1.

The fat of a sample is extracted using a high boiling point and relatively polar solvent. The term high boiling point means that the solvent, compared with customary extraction agents, possesses a high boiling point and thus will extract all the fats contained in the sample. By selecting such a solvent, a reduction in extraction time will also be attained.

At the same time, the extracted fat is saponified with the aid of a base. With that, the salts of the fatty acids will be formed. A sample of the reaction product obtained in this way can be subjected to analysis, by which means, from the point of view of the physiology of nutrition, a definitive determination of the fat level in the original organic sample is possible.

Through the addition of an aqueous, acidic salt solution, the reaction product Will separate into an aqueous and, in an upper layer, into an organic phase, said upper phase containing the free fatty acids. In order to carry out analysis of the reaction product and determine the total content of fatty acids, a sample is taken from the organic layer.

An advantageous method of analysis will result if the individual constituents of the reaction product are separated from one another for subsequent selective analysis. This is necessary, on the one hand in order to separate the fatty acids from the solvent, and on the other hand also has the advantage that the individual fatty acids will separate from each other and from other, unwanted constituents. The use of a relatively polar, high boiling point solvent will mean that portions are extracted from the sample that do not belong to the actual fats. These constituents can be higher fatty alcohols, dyes or products that arise only during the extraction reaction. Simultaneous detection of these substances during analysis would falsify the measurement results.

Preferably, the different constituents of the reaction product are separated by means of gas chromatography. Because the invention intends to determine not the individual fatty acids, but the total of all fatty acids in the sample, a gas chromatograph can be used with a comparatively short separation column, typically 30 cm in length. By selecting such a short separation column, the time required for separation by means of chromatography can be considerably reduced.

In order to detect the different constituents obtained by the separation procedure, a flame ionisation detector (FID) is used.

In order to quantitatively determine the fat content in the sample, an internal standard is added to the sample prior to extraction. An internal standard is a fatty acid that does not occur in natural fats, for example a tridecanic acid (C13 acid), said fatty acid advantageously possessing a similar behaviour to natural fatty acids with regard to detection with an FID. If, prior to extraction, an exactly known amount of internal standard is mixed with the organic sample, the known internal standard can be detected on the spectral distribution of fatty acids. The internal standard is thus a fatty acid used for the calibration of the measurement to permit quantitative determination of fatty acids in the sample. The total portion of fat in the organic sample will be ascertained through integration of the spectrum of the different constituents of the reaction product in the area of the relevant fatty acids, and consideration of the internal standard in order to calculate the absolute value of the fat content.

For extraction of the fat, butanol is preferably used as solvent. Butanol has a boiling point of approximately 117° C.

Preferably, the boiling point anyway lies between 110° C. and 120° C.

Potassium hydroxide is preferably used as a base for the saponification of the dissolved-out fat portion. The use of sodium hydroxide is also conceivable.

For acidification of the saponified fat, preferably an aqueous solution with sodium dihydrogen phosphate ($NaH_2PO_4$) and formic acid is used.

The extraction of the sample ensues in a usual extraction vessel. Here, the sample can be added directly to the solvent. The solvent, the organic sample and the base for saponification of the dissolved-out fats are simultaneously contained within the extraction vessel. It is also conceivable to carry out a filter extraction. To this end, the sample is placed in a filter above the solvent and dissolved by the solvent in back-flow. The addition of the acidic salt solution for acidification of the saponified fat portion ensues in the extraction vessel. The time required for determination of the fat level in a sample is considerably reduced by this method.

BRIEF DESCRIPTION OF THE DRAWINGS

An embodiment of the invention is more closely explained in the following, with the aid of the drawings, namely.

DESCRIPTION OF THE PREFERRED EMBODIMENT

Figure 1:
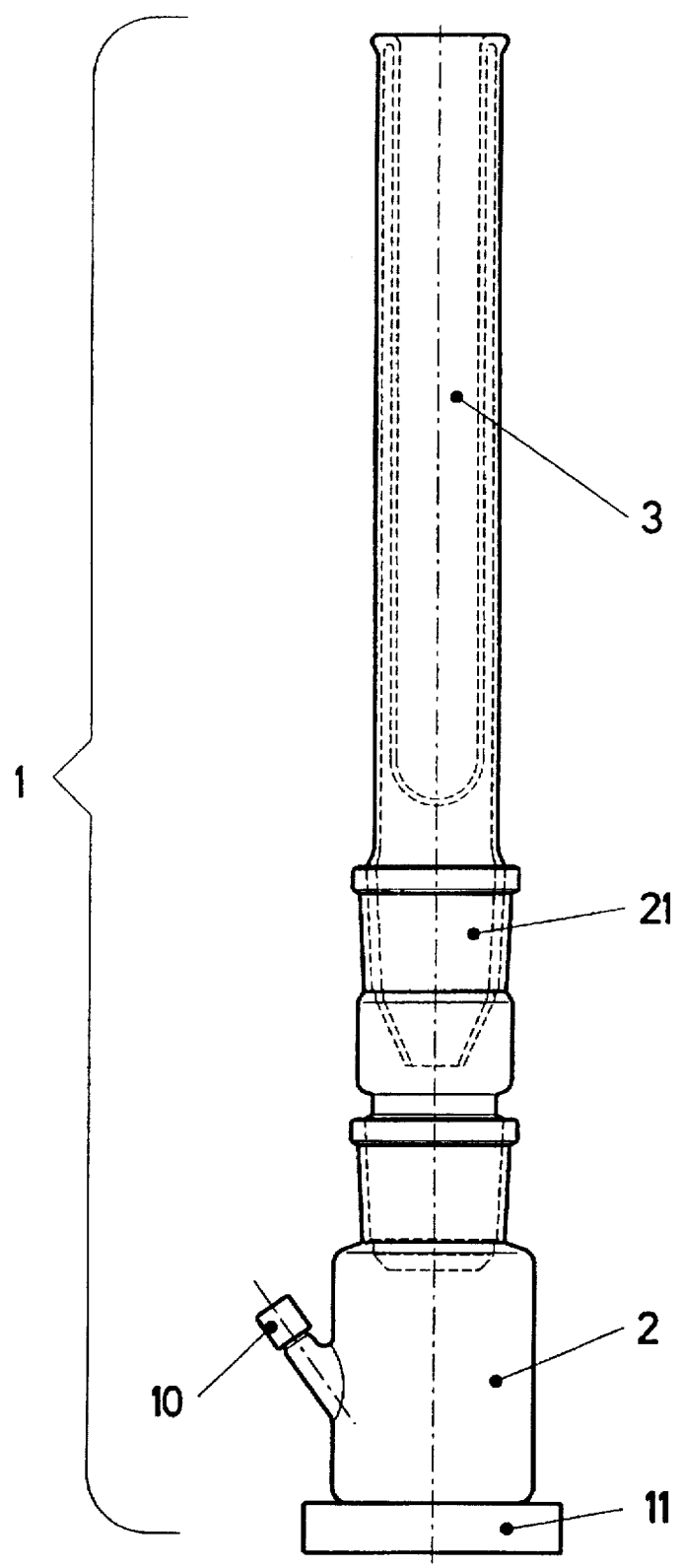
FIG. 1 representation of a glass extraction apparatus.

FIG. 1 shows the glass apparatus of an extractor 1 as can be used for the extraction of fat from an organic sample. The extractor 1 comprises a cooler 3, an intermediate piece 21 for accommodation of the filter containing the sample for extraction, as well as an extraction vessel 2 and a heating device 11 for heating the solvent. In a glass apparatus for carrying out the method according to the invention, the vessel for accommodation of solvent and extracted material also possesses a connection orifice 10 to take out the sample.

Figure 2A:
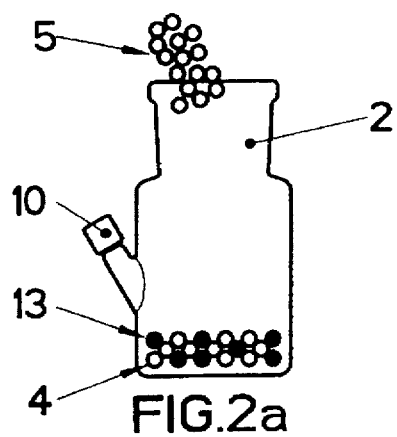
FIGS. 2a to 2f a schematic representation of the stages of the method for determining fat content, FIG. 3 a representation of the spectrum of the measured fatty acids, and FIG. 4a and 4b a schematic representation of two stages of the method using a filter.

FIG. 2a schematically shows a solvent vessel 2 in which, in a preceding step, a sample 4 and an internal standard 13 have been weighed in. Foodstuffs for which the fat content is to be established are generally used as a sample. The internal standard 13 is a fatty acid that does not occur in nature. This can, for example, be a tridecanic or valeric acid. The internal standard 13 and the sample 4 are weighed into the solvent vessel 2. A base material 5 is then likewise weighed into the solvent vessel 2. Potassium hydroxide (KOH) is, for example, suitable as a base.

Figure 2B:
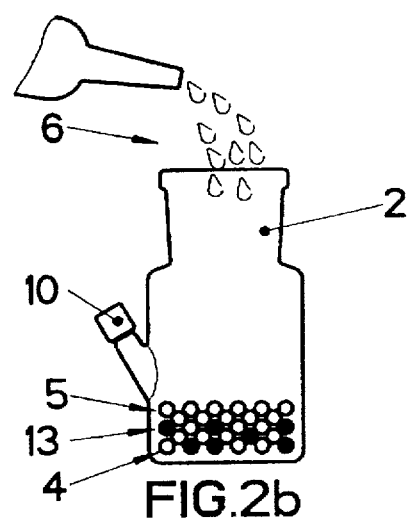

In a next procedural step (see FIG. 2b), a high boiling point solvent 6 is added to the solvent vessel 2. N-butylalcohol, for example, can be used as a high boiling point solvent. In a typical method, 3–5 grams of the sample 4, 0.1 grams of an internal standard 13, 1,5 grams of a base 5 and 45 millilitres of a solvent 6 are used.

Figure 2C:
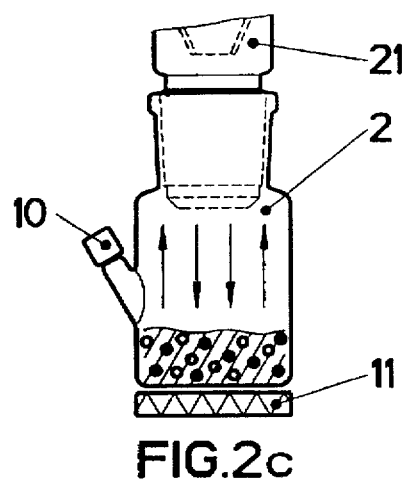
Figure 2D:
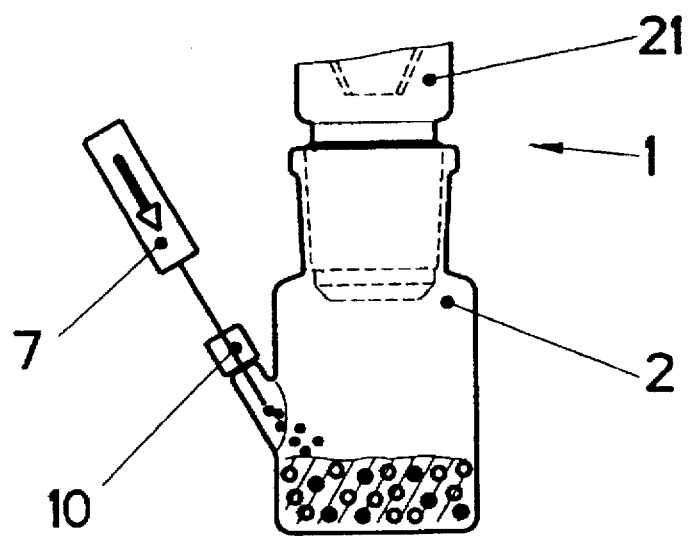
Figure 2E:
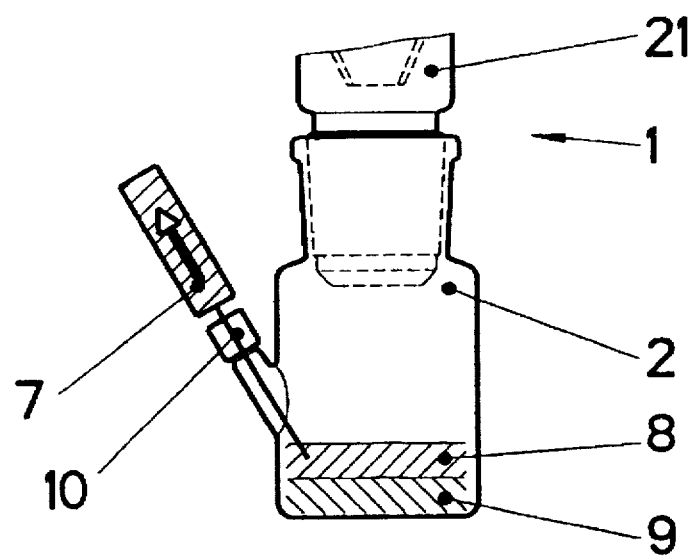

FIG. 2c schematically shows how the solvent vessel 2 is heated by a heating device 11, by which means the solvent will evaporate and will dissolve the fat portions out of the sample along with the internal standard. The fat portion from the sample is extracted at a temperature of at least 100° C., preferably between a temperature of 115° C. and 118° C. When using n-butylalcohol, this extraction will ensue at a temperature of approximately 117° C. (the boiling point of n-butylalcohol). In the same procedural step, the fat portions dissolved out of the sample are saponified in a reaction with the base 5.

The equations for the chemical reactions occurring in this first step of the method are shown in the following. In the actual chemical sense, the applicable fat is ester of the trihedric alcohol glycerin with various fatty acids. Through the reaction with the base, the fat will be saponified, and glycerin and the salts of the fatty acids will be formed.

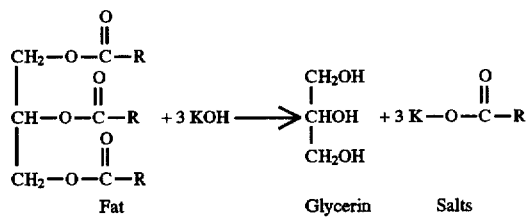

After completion of the extraction, the extraction solution is acidified by addition of an acid salt solution while the solvent is still hot. As an acid salt, sodium dihydrogen phosphate and formic acid can be used, for example. With methods involving the typical values as mentioned above, 40 millilitres of a sodium dihydrogen phosphate solution are added. Through the addition of this acid salt solution, the salts of the fatty acids are converted into the corresponding fatty acids. The chemical reaction taking place in this procedural step is characterized by the following equation:

Two phases will be formed in the extraction vessel through the addition of acid salt solution. An organic phase 8 will be located in the upper portion of the solvent vessel 2, and an aqueous phase 9 will be located at the bottom of the solvent vessel 2. A sample of the reaction product is now taken from the upper phase 8.

Figure 2F:
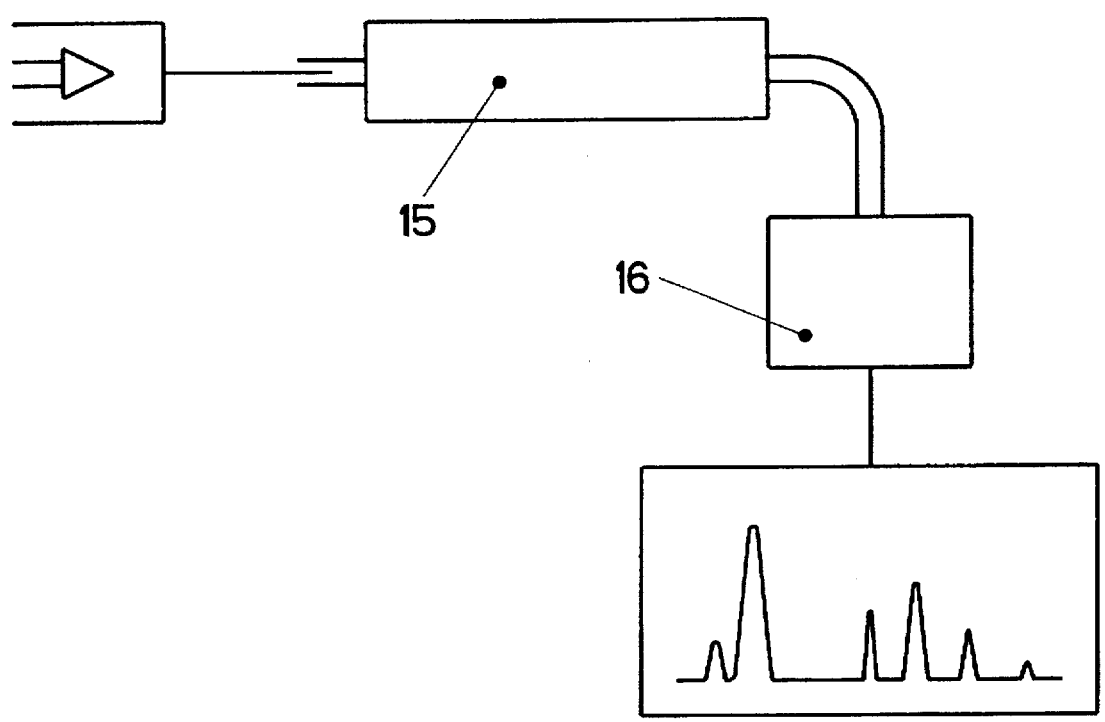

FIG. 2f schematically shows how the sample of the reaction product is placed in a gas chromatograph. Because of their differing molecular properties, the different fatty acids, the solvent molecules as well as further constituents will be separated from each other in a separation tube 15. The molecules arriving at the exit of said separation tube 15 are detected with a flame ionisation detector and traced in the form of a chromatogram. The spectrum represents the amount of molecules arriving at the end of the separation tube, against time. On the basis of the varying speeds that different molecules pass through the separation tube 15, the time axis in the case of homologous bonds becomes a unit for measuring the size of the molecules being registered.

Figure 3:
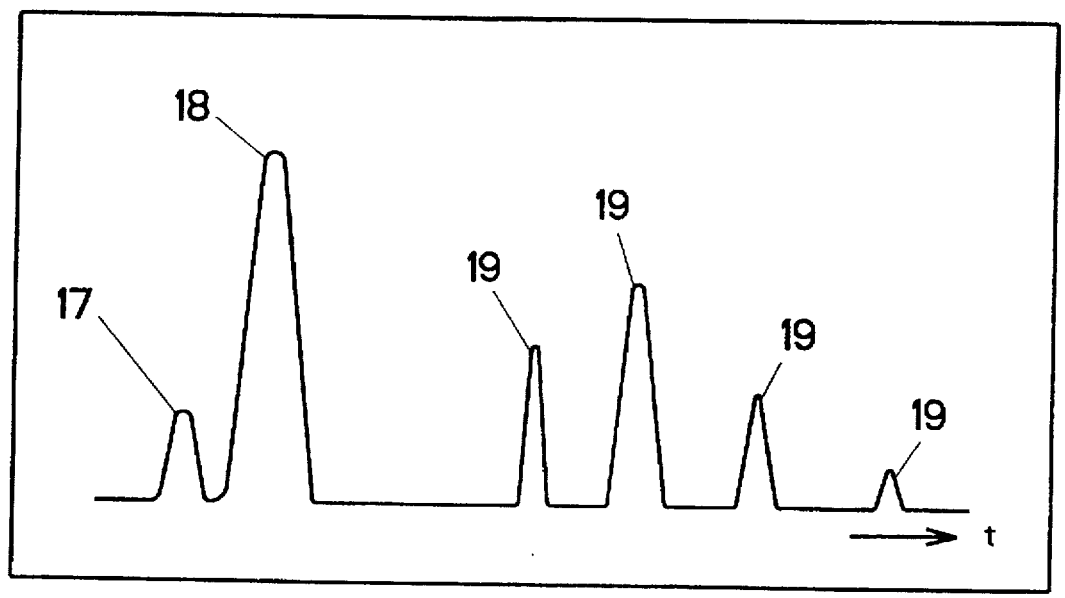

FIG. 3 schematically shows a chromatogram obtained by such a separation and analysis method. During the separation procedure, the molecules of the solvent are the first to be registered and result in a peak 17. The internal standard produces a peak 18 and the different fatty acids create further peaks 19. The total portion of fatty acids in the sample is derived from the sum of all areas delineated within the peaks 19. In order to quantitatively determine the fat content, these surfaces are compared with the area delineated within the peak 18 created by the internal standard. On the basis of the original known amount of internal standard, the total amount of fatty acids in the sample 4 can be deduced.

It is a principle of the invention that, by using a high boiling point solvent, the totality of all fatty acids will be dissolved out of the sample, and that the time required for the extraction will be reduced. The time required for carrying out the measuring procedure is additionally reduced in that saponification of the dissolved-out fat portions is carried out during the actual extraction, and no separation of the basis lines of the peaks 19 is required for determination of the total fat level.

Figure 4A:
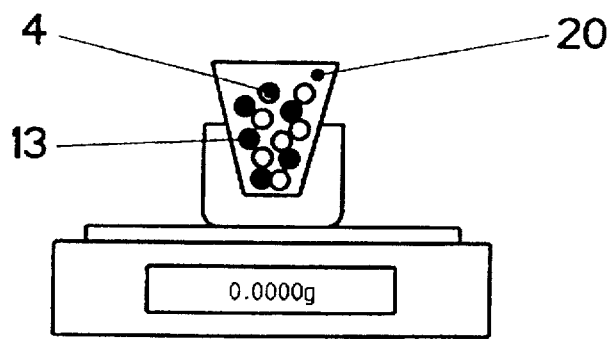

Instead of placing the sample 4 directly into the solvent vessel 2, a filter 20 can also be used to accommodate the sample 4 and the internal standard 13 (see FIG. 4a). The sample 4 and the internal standard 13 are weighed into a filter 20, said filter then being placed into the intermediate piece 21 of the extractor 1.

Figure 4B:
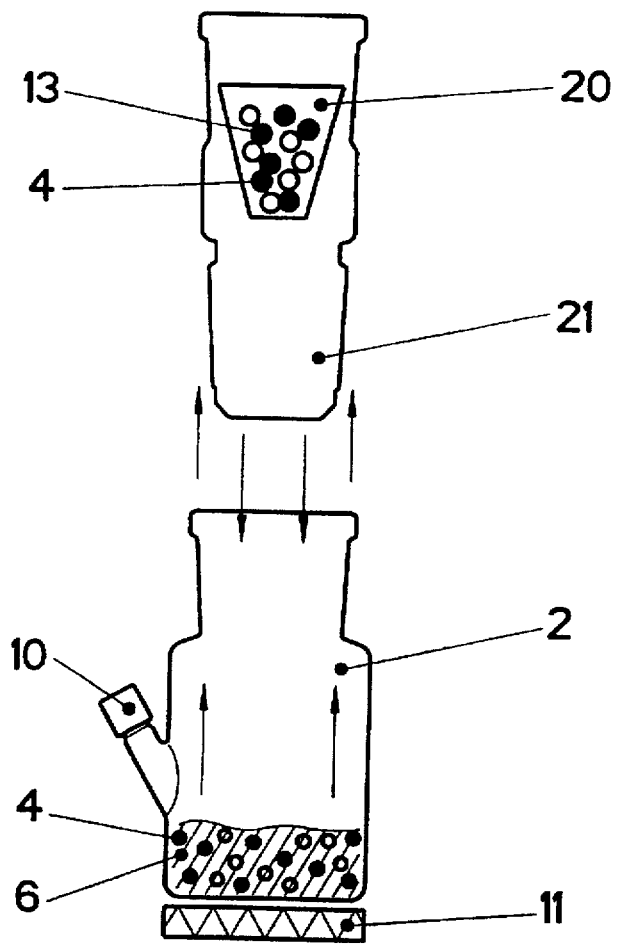

FIG. 4b shows the phase of the filter extraction method corresponding to the direct extraction method as shown in FIG. 2c. The solvent 6 is heated in the solvent vessel 2 with the aid of a heating device 11. The heated solvent evaporates and dissolves the fat portion out of the sample and the internal standard contained in the filter 20. The extraction solution, with the dissolved-out fat portion, drips back into the solvent vessel 2. Further procedural steps in the case of filter extraction ensue in the way featured in FIGS. 2d to 2g.

Inasmuch as the invention is subject to modifications and variations, the foregoing description and accompanying drawings should not be regarded as limiting the invention, which is defined by the following claims and various combinations thereof.

What is claimed is:

1. A method for determining the fat content of a sample, preferable an organic sample, comprising steps of:
    a) extracting a fat portion from the sample at a temperature of at least 100° C. with a solvent having a boiling point of at least 110° C.
    b) simultaneously saponifying the extracted fat portion by means of a base, said saponification yielding salts of fatty acids of the sample as a reaction product,
    c) adding an acid solution to the reaction product to convert the salts of fatty acids into fatty acids of the reaction product, and
    d) analyzing a sample of the reaction product and determining a total content of fatty acids within the organic sample.

2. A method for determining the fat content according to claim 1 wherein the step of extracting the fat portion is at a temperature between 115° C. with a solvent having a boiling point between 110° C. and 120° C.

3. A method for determining the fat content of samples according to claim 2, wherein the acid solution comprises sodium dihydrogen phosphate ($NaH_2PO_4$) and formic acid into fatty acids.

4. A method for determining the fat content of samples according to claim 1, further comprising forming an aqueous phase and an organic containing the reaction product after the addition of the acid solution to the reaction product.

5. A method for determining the fat content of samples according to claim 1, further comprising a step of separating the fatty acids of the reaction product into individual constituents for selective analysis.

6. A method for determining the fat content of samples according to claim 5, further comprising a step of separating the individual constituents of the reaction product by means of a gas chromatography method.

7. A method for determining the fat content of samples according to claim 6, wherein said gas chromatography method employs a separation column with a length of less than 40 cm.

8. A method for determining the fat content of samples according to claim 7, further comprising a step of detecting the individual constituents of the reaction product by means of a flame ionization detector.

9. A method for determining the fat content of samples according to claim 5, further comprising adding an internal standard to the sample prior to extraction and determining the individual constituents of the reaction product, wherein after determination of the individual constituents of the reaction product, the total amount of fatty acids of the sample is determined on the basis of the internal standard.

10. A method for dertermining the fat content of samples according to claim 1, wherein said solvent has a higher polarity than diethylether.

11. A method of determining the fat content of samples according to claim 1, wherein said base comprises potassium hydroxide.

12. A method for determining the fat content of samples according to claim 1, wherein said solvent comprises n-butyl alcohol.

13. A method for determining the fat content of samples according to claim 1 further comprising placing the sample directly in the solvent in order to extract the fat portions from said sample.

14. A method for determining the fat content of samples according to claim 1, further comprising placing the sample in a filter positioned above the solvent and refluxing the solvent in order to extract the fat portion from the sample.

* * * * *